(12) United States Patent
Jones et al.

(10) Patent No.: US 12,089,874 B2
(45) Date of Patent: Sep. 17, 2024

(54) APPARATUS FOR PROVIDING ACCESS FOR A MEDICAL PROCEDURE

(71) Applicant: Titan Medical Inc., Toronto (CA)

(72) Inventors: Evan Rittenhouse Jones, Levittown, NY (US); Maxime Blain, Rosedale, NY (US); Christopher Dean Smith, Shirley, NY (US)

(73) Assignee: Titan Medical Inc., Toronto (CA)

( * ) Notice: Subject to any disclaimer, the term of this patent is extended or adjusted under 35 U.S.C. 154(b) by 0 days.

(21) Appl. No.: 18/149,791

(22) Filed: Jan. 4, 2023

(65) Prior Publication Data

US 2023/0248390 A1 Aug. 10, 2023

Related U.S. Application Data

(63) Continuation of application No. 17/142,564, filed on Jan. 6, 2021, now Pat. No. 11,553,944, which is a
(Continued)

(51) Int. Cl.
*A61B 17/34* (2006.01)
*A61B 17/00* (2006.01)
(Continued)

(52) U.S. Cl.
CPC .......... *A61B 17/3423* (2013.01); *A61B 17/29* (2013.01); *A61B 17/3474* (2013.01);
(Continued)

(58) Field of Classification Search
CPC ........ A61B 2017/3419; A61B 17/3423; A61B 17/3474; A61B 2017/3486; A61B 17/29;
(Continued)

(56) References Cited

U.S. PATENT DOCUMENTS

| 5,634,911 A | * | 6/1997 | Hermann ........... A61B 17/3423 |
| | | | 604/246 |
| 7,862,554 B2 | | 1/2011 | Hegeman |

(Continued)

FOREIGN PATENT DOCUMENTS

CA 2749022 4/2012

OTHER PUBLICATIONS

Definition of Conduit—https://www.dictionary.com/browse/conduit?s=t (Year: 2020).*
(Continued)

*Primary Examiner* — Michael J Tsai
*Assistant Examiner* — Rachel T. Smith
(74) *Attorney, Agent, or Firm* — Knobbe, Martens, Olson & Bear, LLP

(57) ABSTRACT

In some embodiments an apparatus for providing access for a medical procedure in a patient's body cavity includes a stem configured for insertion through an opening in a body cavity wall. The stem has a bore and a cap is disposed at a proximal end thereof and includes an entry port in communication with the bore which receives an instrument to be inserted into the body cavity. An inflatable annular seal is disposed on the stem proximate the cap and a conduit extends through the cap providing pressurized gas at a first outlet in fluid communication with the body cavity providing insufflation pressure. A second outlet of the conduit is in fluid communication the seal, which when disposed inside the body cavity proximate the wall and inflated by pressurized gas, bears on an inner surface of the wall urging the cap into contact with an outer surface of the wall while sealing the opening.

19 Claims, 4 Drawing Sheets

Related U.S. Application Data continuation of application No. 16/235,288, filed on Dec. 28, 2018, now Pat. No. 10,905,464.

(51) Int. Cl.
*A61B 17/29* (2006.01)
*A61B 18/00* (2006.01)

(52) U.S. Cl.
CPC ............... *A61B 2017/00557* (2013.01); *A61B 2017/3419* (2013.01); *A61B 2017/3454* (2013.01); *A61B 2017/3486* (2013.01); *A61B 2018/00595* (2013.01); *A61B 2018/00601* (2013.01); *A61B 2217/005* (2013.01); *A61B 2217/007* (2013.01)

(58) Field of Classification Search
CPC .. A61B 2017/00557; A61B 2017/3454; A61B 2018/00595; A61B 2018/00601; A61B 2217/005; A61B 2217/007; A61B 18/1482; A61B 2017/3441; A61B 2017/3445; A61M 2017/3486; A61M 25/09041; A61M 25/01
See application file for complete search history.

(56) References Cited

U.S. PATENT DOCUMENTS

| | | | |
|---|---|---|---|
| 2004/0111061 A1* | 6/2004 | Curran | A61B 17/3421 604/174 |
| 2006/0224174 A1 | 10/2006 | Smith et al. | |
| 2010/0228094 A1 | 9/2010 | Ortiz et al. | |
| 2010/0312066 A1* | 12/2010 | Cropper | A61B 17/3423 600/207 |
| 2012/0004613 A1* | 1/2012 | Franer | B65B 55/12 604/167.03 |
| 2012/0190932 A1 | 7/2012 | Okoniewski | |
| 2013/0137932 A1* | 5/2013 | Piech | A61B 17/3423 600/204 |
| 2020/0205854 A1 | 7/2020 | Jones et al. | |
| 2022/0008064 A1* | 1/2022 | Heneveld | A61B 17/3423 |

OTHER PUBLICATIONS https://www.merriam-webster.com/dictionary/toroid (Year: 2023).*
Applied Medical, Kii Balloon Blunt Tip System, downloaded on Dec. 27, 2018, in 2 pages.
Applied Medical, Kii Access Systems, 2017, in 8 pages.

* cited by examiner

APPARATUS FOR PROVIDING ACCESS FOR A MEDICAL PROCEDURE

BACKGROUND

1. Field

This disclosure relates to apparatus used for surgical procedures and more particularly to providing access to a body cavity of a patient for robotic and/or laparoscopic surgical instruments and equipment during a medical or surgical procedure.

2. Description of Related Art

In robotic and laparoscopic surgery it is common to provide access to a body cavity of a patient through an access device. An incision is typically made in a wall of the body cavity and the access device is inserted into the incision to provide a sealed entry point for a surgical device such as a laparoscopic instrument. For robotic and laparoscopic surgery the access device may be required to provide a seal to any instrument inserted into the body cavity through the access device. The seal maintains insufflation pressure in the body cavity during insertion and subsequent movement of the instrument. The access device may also be configured to act in the removal of smoke produced during electrocauterization of tissues within the body cavity.

Commonly available access devices include surgical trocars such as those manufactured by Covidien PLC of Dublin, Ireland, Stryker Corporation of Michigan, USA, and/or Applied Medical of California, USA.

SUMMARY

In accordance with some embodiments there is provided an apparatus for providing access for a medical procedure in a body cavity of a patient. The apparatus includes a stem operably configured to be inserted through an opening in a wall of the body cavity, the stem having a bore extending therethrough. The apparatus also includes a cap disposed at a proximal end of the stem, the cap including an entry port in communication with the bore configured to receive an instrument to be inserted through the bore into the body cavity. The apparatus further includes an inflatable annular seal disposed on the stem proximate the cap and a conduit extending through the cap. The conduit includes an inlet in the cap operable to connect to a source of pressurized gas and a first outlet disposed to be in fluid communication with the body cavity after the stem is inserted through the opening in the wall of the body cavity. The first outlet is operable to provide an insufflation pressure to the body cavity. The conduit also includes a second outlet in fluid communication with the seal. The seal, when disposed inside the body cavity proximate the wall and inflated by the pressurized gas, bears on an inner surface of the wall urging the cap into contact with an outer surface of the wall while sealing the opening.

The entry port may include a displaceable seal operable to seal the entry port to maintain the insufflation pressure and prevent contamination of the body cavity after the stem is inserted into the opening in the wall of the body cavity.

The stem may include a tip including at least one cutting edge operable to form the opening by piercing the wall of the body cavity.

The opening in the wall of the body cavity may include one of an incision and a natural orifice in communication with the body cavity.

Prior to insertion of the stem, the seal may be in an initially deflated condition facilitating insertion of the stem through the opening.

The seal may be fabricated from a compliant material having sufficient elasticity to return to the initially deflated condition when deflated prior to removal of the apparatus from the wall of the body cavity.

The apparatus may include an inflatable annular instrument seal disposed at a distal end of the stem, and when the instrument is inserted through the bore and projects beyond the distal end of the stem into the body cavity, the seal, when inflated, provides a seal between a portion of the distal end of the stem and outer surfaces of the instrument.

The apparatus may, include a partition within the bore dividing the bore into a plurality of channels extending therethrough, each of the plurality of channels being operable to receive an instrument to be inserted into the body cavity.

The partition may extend beyond a distal end of the stem and may also extend outwardly from the opening in the cap and the partition may include a central portion and a plurality of peripherally formed open channels configured to receive the plurality of instruments.

The instrument may include at least one of an instrument for grasping, manipulating, cauterizing, or cutting tissue, an instrument for providing an interior view of the body cavity, and an instrument for providing or removing fluid from the body cavity.

In accordance with some embodiments there is provided an apparatus for providing access for a medical procedure in a body cavity of a patient. The apparatus includes a stem operably configured to be inserted through an opening in a wall of the body cavity, the stem having a bore extending therethrough. The apparatus also includes a cap disposed at a proximal end of the stem, the cap including an entry port in communication with the bore configured to receive an instrument to be inserted through the bore into the body cavity. The apparatus further includes an inflatable instrument seal disposed at a distal end of the stem. A conduit extends through the cap and is in fluid communication with the instrument seal and operable to inflate the seal. When the instrument is inserted through the bore and protrudes beyond the distal end of the stem into the body cavity, the instrument seal surrounds the instrument and when inflated, provides a seal between a portion of the distal end of the stem and outer surfaces of the instrument.

The conduit may include an inlet disposed on the cap configured to receive a pressurized fluid operable to inflate the instrument seal.

The pressurized fluid may include a liquid solution injected through the inlet into the conduit and the conduit may further include a valve operably configured to retain the pressurized fluid within the annular seal and conduit once injected into the inlet.

The inlet may be operable to connect the conduit to a source of pressurized gas.

The apparatus may include an inflatable annular retaining seal disposed on the stem proximate the cap and in fluid communication with the conduit for inflating the seal. The retaining seal, when disposed inside the body cavity proximate the wall and inflated by the pressurized gas, bears on an inner surface of the wall urging the cap into contact with an outer surface of the wall while sealing the opening.

The conduit may include an outlet disposed to be in fluid communication with the body cavity after the stem is inserted through the opening in the wall of the body cavity, the first outlet being operable to provide an insufflation pressure to the body cavity.

The instrument seal and the retaining seal may be fabricated from a compliant material having sufficient elasticity to return to the initially deflated condition when deflated prior to removal of the apparatus from the wall of the body cavity.

The apparatus may include a partition within the bore dividing the bore into a plurality of channels extending therethrough, each of the plurality of channels being operable to receive an instrument to be inserted into the body cavity.

The partition extends beyond a distal end of the stem and also extends outwardly from the opening in the cap and the partition may include a central portion and a plurality of peripherally formed open channels for receiving the plurality of instruments.

The instrument seal may have a generally toroidal shape when inflated.

The apparatus may be configured to accommodate a plurality of instruments within the bore and the instrument seal may include a plurality of bulged regions disposed to bear on an outer surface of each instrument to provide increased force for holding the instruments within the bore when the seal is inflated.

The instrument may include at least one of an instrument for grasping, manipulating, cauterizing, or cutting tissue, an instrument for providing an interior view of the body cavity, and an instrument for providing or removing fluid from the body cavity.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
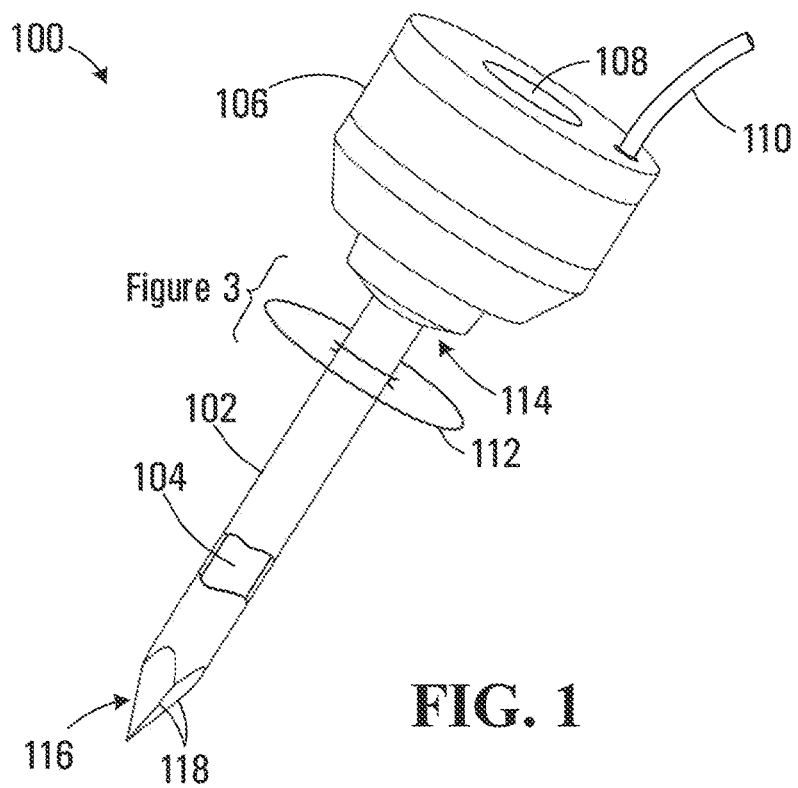
FIG. 1 is a perspective view of an apparatus for providing access for a medical procedure in a body cavity of a patient.

Referring to FIG. 1, an apparatus for providing access for a medical procedure in a body cavity of a patient is shown generally at 100. The apparatus 100 includes a stem 102 operably configured for insertion through an opening in a wall of the body cavity of a patient. The stem 102 has a bore 104 extending through the stem and the apparatus 100 includes a cap 106 disposed at a proximal end of the stem. The cap 106 has an entry port 108 in communication with the bore 104 for receiving an instrument (not shown in FIG. 1) to be inserted through the bore into the body cavity. The cap 106 has an inlet 110 for connecting to a pressurized source (not shown in FIG. 1).

The apparatus 100 also includes an annular inflatable seal 112 on the stem 102 proximate the cap 106. In this embodiment the seal 112 is disposed at a location on the stem 102 spaced apart from an underside 114 of the cap 106. The seal 112 as shown in FIG. 1 is in an uninflated condition and the apparatus 100 is ready for insertion into a body cavity of the patient.

Figure 2:
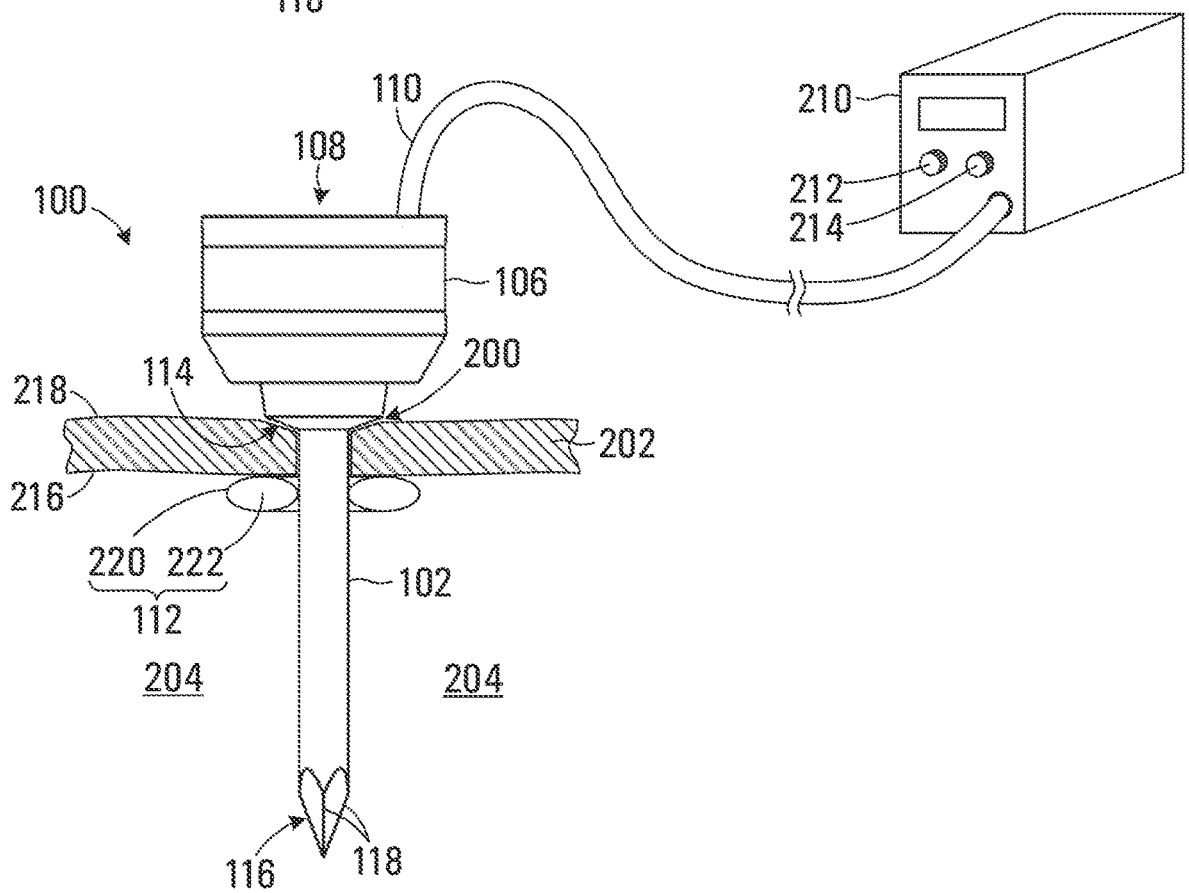
FIG. 2 is a side view of the apparatus shown in FIG. 1 inserted into an opening in a body wall of a patient.

Referring to FIG. 2, the stem 102 may be inserted through an opening 200 in a wall 202 of a body cavity 204 of a patient for performing a surgical or other medical procedure. As an example, the body cavity 204 may be an abdominal cavity and the wall 202 may be an abdominal wall. In some embodiments the opening 200 may be an incision made by a surgeon to permit access to the underlying body cavity 204. Alternatively the apparatus 100 shown in FIG. 1 includes a tip 116 having cutting edges 118 and the tip may be used in some embodiments to form the necessary opening by piercing the wall 202 of the body cavity 204. In other embodiments the opening 200 may be a natural orifice that permits access to a body cavity 204 of the patient.

Prior to insertion of the stem 102, the seal 112 would be in an initially deflated condition to facilitate insertion of the stem through the opening 200. The seal 112 is configured as an annular balloon having a compliant wall 220 enclosing an interior volume 222. When the seal 112 is deflated the complaint wall 220 will deflect during insertion to lie generally along a portion of the stem 102 proximate the underside 114 of the cap 106. The compliant wall 220 may be fabricated from a material having sufficient compliance to easily deflect during insertion when uninflated. Materials such as polyurethane or silicone may be used to fabricate the seal 112. The entry port 108 may include a displaceable seal (not shown) that is operable to seal off the bore 104 to reduce escapement of insufflation gas and to prevent contamination of the body cavity 204 prior to an instrument being inserted through the entry port into the body cavity.

Figure 3:
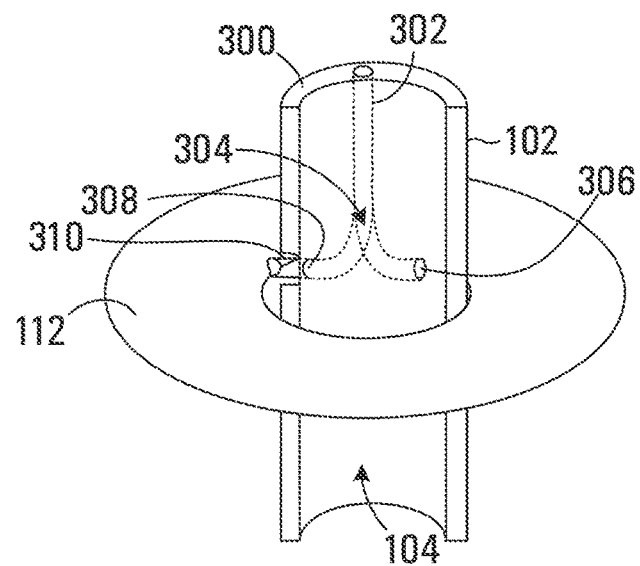
FIG. 3 is a perspective view of a portion of the apparatus shown in FIG. 1 and FIG. 2.

The seal 112 and a portion of the stem 102 in cut-away view are shown in more detail in FIG. 3. The stem 102 (shown truncated in FIG. 3) has a tubular wall 300 that accommodates a conduit 302. In this embodiment the conduit 302 bifurcates at a location 304 to provide a first outlet 306 in fluid communication with the bore 104. The first outlet 306 would thus also be in fluid communication with the body cavity after the stem 102 is inserted through the opening 200 in the wall 202 of the body cavity 204. In other embodiments the first outlet 306 may be disposed elsewhere within the bore 104.

The conduit 302 also includes a second outlet 308 in fluid communication with a neck 310 of the seal 112 that provides fluid communication with the interior volume 222 of the seal. The neck 310 extends through a passage in the tubular wall 300, and is shown with the tubular wall partially cut away in FIG. 3. In other embodiments, separate conduits may be provided such that a first conduit includes the first outlet 306 and a second conduit includes the second outlet 308.

Referring back to FIG. 2, prior to or immediately following insertion of the apparatus 100 through the opening 200 in the wall 202, the inlet 110 may be connected to an insufflation source 210. The insufflation source 210 may be configured to deliver a controlled flow of a gas such as carbon dioxide ($CO_2$) for causing insufflation of the body cavity 204. The insufflation source 210 includes a control 212 for setting a desired insufflation pressure and a control 214 for setting a desired fluid flow rate for maintaining a desired insufflation of the body cavity 204. When the insufflation source 210 is connected and in operation, the seal 112 is inflated though the neck 310 by the insufflation gas pressure and the complaint wall 220 of the seal bears on an inner surface 216 of the body, wall 202. When inflated the seal 112 takes on a generally toroidal shape and urges the underside 114 of the cap 106 into contact with an outer surface 218 of the body wall while sealing the opening 200 to prevent escapement of the insufflation gas. The inflated seal 112 may also act to staunch bleeding from the incision, both into the body cavity 204 and above the opening 200. The use of the insufflation source 210 to both inflate the seal 112 and provide insufflation has an advantage of causing the seal 112 to provide a controlled force at the opening 200 that matches the pressure within the body cavity 204. If the seal 112 were to be overinflated, damage to tissues of the wall 202 may result which may extend a post-surgery healing time and may also increase the risk of infection. In other embodiments, one insufflation source such as shown at 210 may be used to deliver pressurized gas for inflating the seal 112 and another insufflation source or a multiple output insufflation source may be used to provide an independent gas flow for insufflating the body cavity 204.

In the embodiment shown in FIG. 3, the conduit 302 is integral with the tubular wall 300 of the stem 102. However in other embodiments the conduit 302 may be provided by a tube extending through the tubular wall 300 or extending along a side of the bore 104.

Once inserted through the opening 200 and placed under insufflation pressure by the insufflation source 210, the apparatus 100 is retained in place and provides access for various instruments to be inserted through the entry port 108 and the bore 104 into the body cavity 204. Any of a variety of instruments may be deployed for performing operations within the body cavity 204 including laparoscopic or robotic instruments such as dissectors or forceps, cauterizing tools, imaging devices for providing a view inside the body cavity, and devices for introducing or removing fluids from the body cavity.

Once the operation within the body cavity 204 is completed, the instruments may be removed and the insufflation pressure reduced or removed, causing the seal 112 to deflate. The seal may be fabricated from a material having sufficient elasticity to return to substantially the initially deflated condition when the inflation pressure is removed, facilitating removal of the apparatus 100 from the wall 200 of the body cavity 204.

Figure 4:
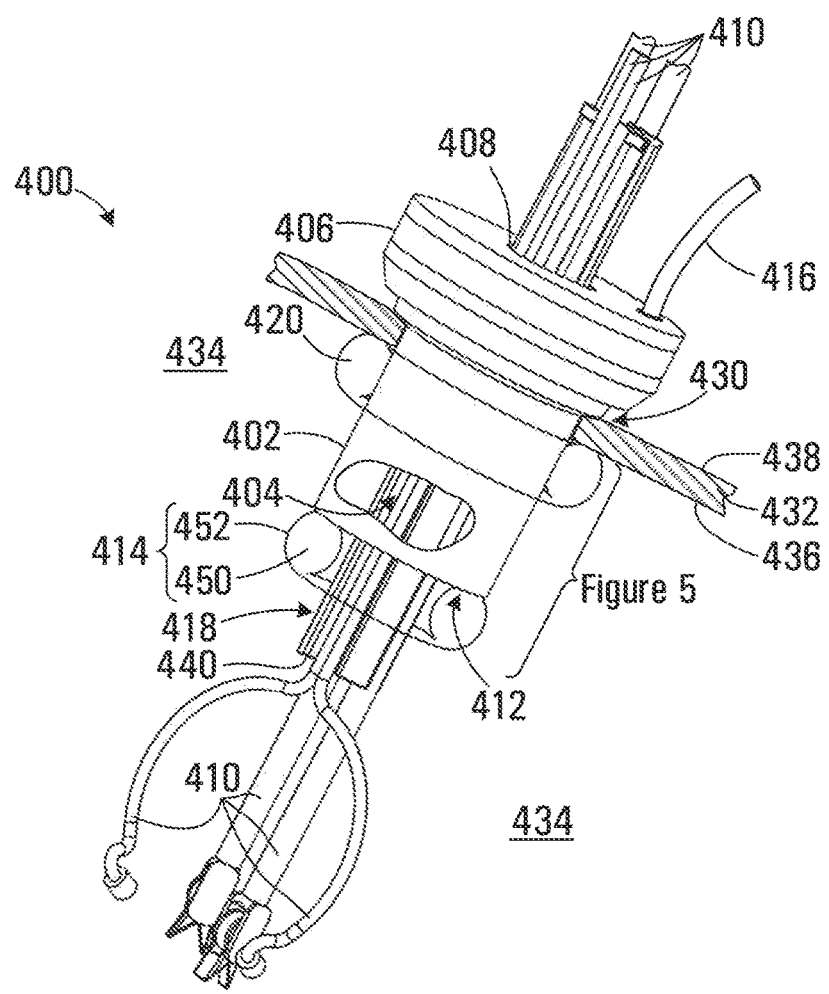
FIG. 4 is a perspective view of another embodiment of an apparatus for providing access for a medical procedure in a body cavity of a patient.

Referring to FIG. 4, an apparatus for providing access for a medical procedure in a body cavity of a patient in accordance with another embodiment is shown at 400. The apparatus 400 includes a stem 402 that has been inserted through an opening 430 in a wall 432 of a body cavity 434 of a patient. The stem 402 has a bore 404 extending through the stem and the apparatus 400 includes a cap 406 disposed at a proximal end of the stem. The cap 406 has an entry port 408 on the cap 406 and in this embodiment a plurality of instruments 410 are shown extending through the entry port and cap 406. The plurality of instruments 410 also protrude slightly from a distal end 412 of the stem 402. The instruments 410 may include instruments for grasping, manipulating, cauterizing, or cutting tissue, instruments for providing an interior view of the body cavity, and/or instruments for providing or removing fluid from the body cavity. The instruments 410 may be configured for laparoscopic and/or robotic surgery processes.

The apparatus 400 also includes an inflatable instrument seal 414 disposed at the distal end 412 of the stem 402. The inflatable instrument seal 414 is configured as an annular balloon having an interior volume 450 enclosed within a complaint wall 452 for containing a pressurized fluid.

Figure 5:
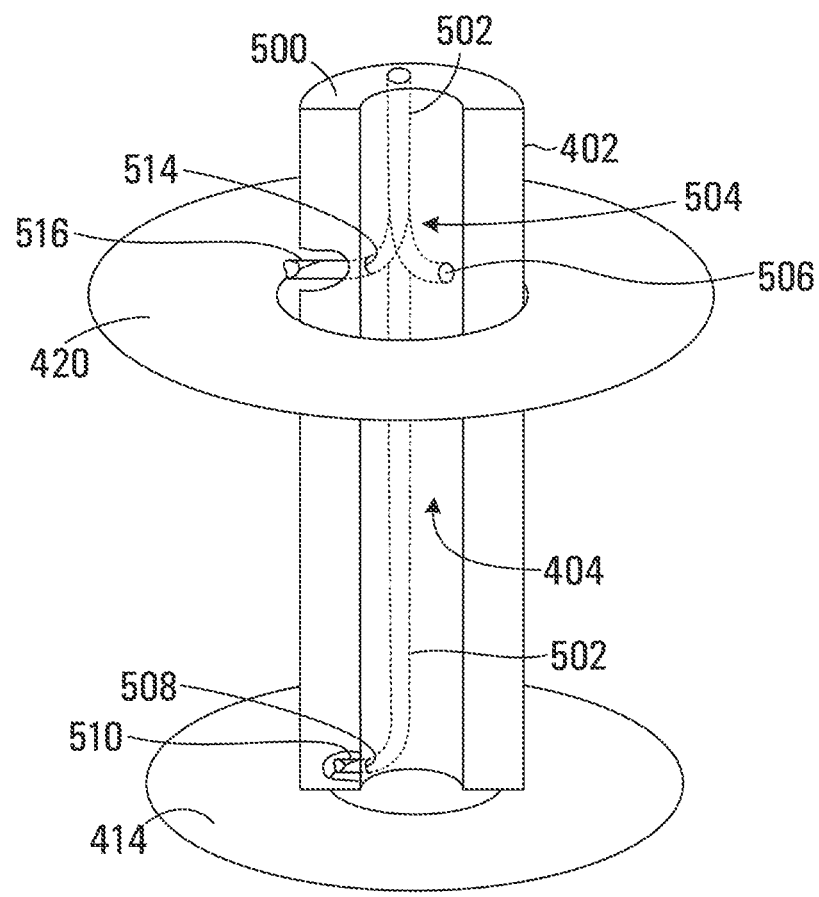
FIG. 5 is a perspective view of a portion of the apparatus shown in FIG. 4.

The instrument seal 414 and a portion of the stem 402 in cut-away view are shown in more detail in FIG. 5. Referring to FIG. 5, the stem 402 has a tubular wall 500 that accommodates a conduit 502. In the embodiment shown, the conduit 502 divides at a location 504 to provide a first outlet 506 in fluid communication with the bore 404. When the stem 402 is inserted through the opening 430, the first outlet 506 would thus be in fluid communication with the body cavity 434. The conduit 502 also includes a second outlet 508 in fluid communication via a neck 510 with the interior volume 450 of the instrument seal 414. The neck 510 extends through the tubular wall 500, which is shown cut away in FIG. 5. In other embodiments, separate conduits may be provided such that a first conduit includes the first outlet 506 and a second conduit includes the second outlet 508.

Referring back to FIG. 4, the apparatus 400 also includes an inlet 416 on the cap 406 for connecting to an insufflation source, such as shown at 210 in FIG. 2. The inlet 416 is in fluid communication with the conduit 502. Prior to insertion of the apparatus 400 through the opening 430 in the body wall 432, the instrument seal 414 is maintained in a deflated condition. Following insertion of the apparatus 400 the instruments 410 may inserted through the bore 404 to protrude beyond the distal end 412 of the stem 402 into the body cavity 434. The inlet 416 may then be connected to an insufflation source or if already connected the source may be activated and the instrument seal 414 inflated as shown in FIG. 4. The instrument seal 414, when inflated expands to provide a seal between a portion of the distal end 412 of the stem 402 and outer surfaces 418 of the instruments 410. The instrument seal 414 may be fabricated from a compliant material that when inflated takes on a generally toroidal shape and causes the complaint wall 452 to bear on the outer surfaces 418 of the instruments 410. The inflated inflatable instrument seal 414 may also hold the instruments in place within the bore 404 to at least some extent by bearing against the instrument. In one embodiment the complaint wall 452 of the inflatable instrument seal 414 may be fabricated such that surfaces of the seal that bear on the instruments 410 have increased surface friction to assist with holding the instruments in place. The instrument seal 414 also functions to prevent body fluids from the body cavity 434 from entering the bore 404.

In the embodiment shown in FIG. 4 and FIG. 5, the apparatus 400 also includes an inflatable annular retaining seal 420 disposed on the stem 402 proximate the cap 406. The retaining seal 420 is similarly configured and operates generally as described above in connection with the seal 112 in the embodiment shown in FIG. 1-FIG. 3. Referring to FIG. 5, the conduit 502 also includes a third outlet 514 in fluid communication via a neck 516 with the interior volume of the retaining seal 420. The neck 516 extends through a passage in the tubular wall 500, shown in cut away view in FIG. 5. The retaining seal 420, when disposed inside the body cavity 434 proximate the body wall 432 and inflated by pressurized gas, bears on an inner surface 436 of the body wall 432 urging the cap 406 into contact with an outer surface 438 of the wall. In some embodiments, a separate conduit may be provided such that a third conduit includes the third outlet 514.

In the embodiment shown in FIG. 5, inflation of the retaining seal 420 is via a pressurized gas supplied through the conduit 502. However in other embodiments, the retaining seal 420 and instrument seal 414 may be inflated by introducing a liquid solution such as saline into the seals 414 and 420 via a separate conduit that is not associated with the body cavity insufflation. When using a liquid solution to inflate the seals 414 and 420, the conduit through which the liquid is introduced may include a valve operably configured to retain the liquid within the seals once injected. In other embodiments, the retaining seal 420 and instrument seal 414 may be inflated by introducing separate gases into the seals 414 and 420 via one or more separate conduits that are not associated with the body cavity insufflation.

When the liquid solution or the pressurized gas supply is removed, the respective interior volumes of the instrument seal 414 and retaining seal 420 are deflated and have sufficient elasticity to return to their initially deflated condition for removal of the apparatus 400 from the wall 432 of the body cavity 434.

Figure 6:
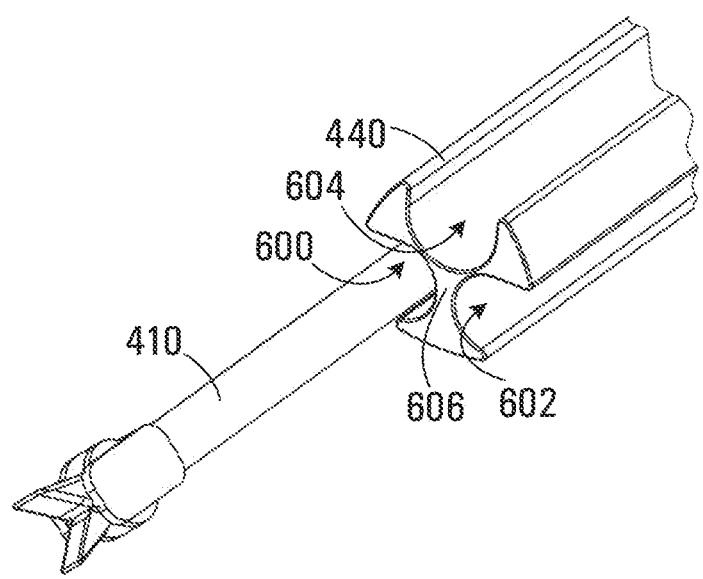
FIG. 6 is a perspective view of a partition received within the bore of the apparatus shown in FIG. 4.

In the embodiment shown in FIG. 4, the apparatus 400 includes a partition 440 disposed within the bore 404. Referring to FIG. 6, the partition 440 has a plurality of channels 600, 602, and 604 sized to receive the various instruments 410, one of which is shown. In this embodiment, the partition 404 includes a central portion 606 and the channels are open at a peripheral for receiving the instruments 410. The partition 440 is configured to be removable from the bore 404, but in other embodiments may be integral with the bore.

Figure 7:
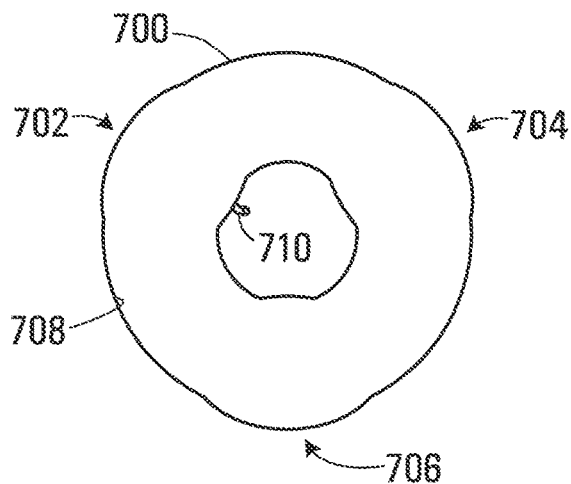
FIG. 7 is a plan view of an instrument seal in accordance with another embodiment.
Figure 8:
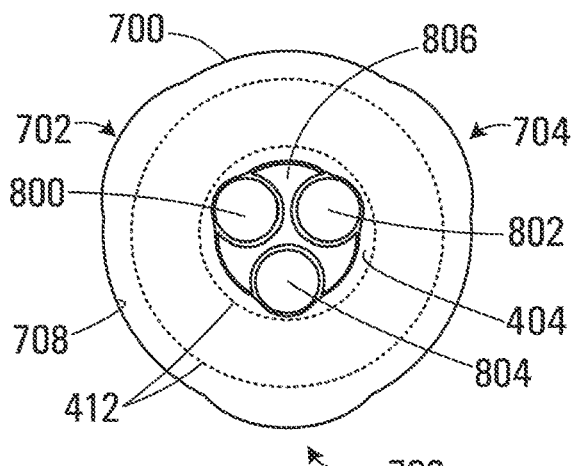
FIG. 8 is a plan view of the instrument seal shown in FIG. 7 installed on the apparatus shown in FIG. 4.

As disclosed above the seals 112 and 414 may have a generally toroidal shape when inflated. Referring to FIG. 7, in some embodiments the instrument seal 414 may be fabricated such that when inflated it has a non-circular cross section as shown at 700. The seal 700 has 3 bulged regions 702, 704, and 706, which may be accomplished by selectively thinning a wall 708 of the seal in the bulged regions with respect to other wall regions. Alternatively, the seal 700 may be shaped such that the bulged regions 702, 704, and 706 are also present when the seal is uninflated. The seal 700 has an inlet 710 for inflating the seal. Referring to FIG. 8, the seal 700 is shown deployed at distal end 412 of the stem 402 (shown in FIG. 4). In this embodiment three instruments 800, 802, and 804 are accommodated within the bore 404 of the apparatus 400 in channels provided by a partition 806. When the seal 700 is inflated, the seal bears on the partition 806, thus exerting a force that seals to the partition. The seal 700 also bears on the instruments 800, 802, and 804, exerting an increased force on the instruments at the bulged regions 702, 704, and 706. The increased force at the bulged regions 702, 704, and 706 provides an additional retaining force for holding the instruments in place within the bore 404.

Figure 9:
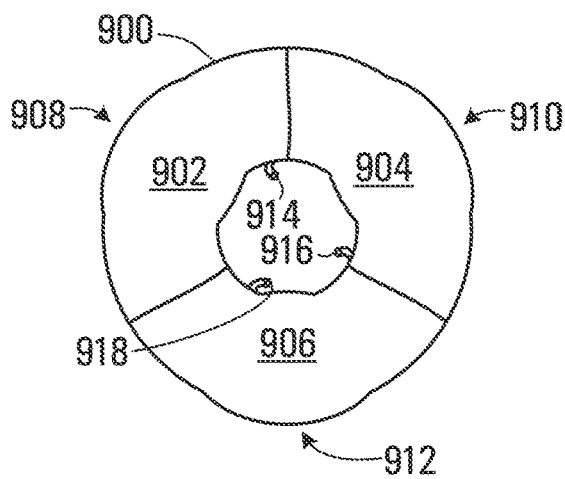
FIG. 9 is a plan view of an instrument seal in accordance with a further embodiment.

Referring to FIG. 9, in some embodiments a seal 900 may be shaped generally as shown in FIG. 7, but with an inner volume of the seal being partitioned into a plurality of volumes 902, 904, 906 generally corresponding to bulged regions 908, 910, and 912. Each of the volumes 902, 904, 906 of the seal 900 has a respective separate inlet 914, 916, and 918 for separately inflating the seal volumes.

The embodiments disclosed above provide a sealing function and/or retaining function for retaining the apparatus within an opening in the wall of a body cavity or retaining and sealing instruments. In some embodiments, the inflation of the various seals is provided via an already existing insufflation system, which is usually activated during a timeframe when the seals would also be inflated. These embodiments are thus relatively simple to operate in that no additional equipment is required and once the insufflation is no longer required and can be removed, the seals deflate allowing the apparatus to be easily withdrawn.

While specific embodiments have been described and illustrated, such embodiments should be considered illustrative only and not as limiting the disclosed embodiments as construed in accordance with the accompanying claims.

What is claimed is:

1. A method of providing access for a medical procedure in a body cavity of a patient, the method comprising:
   inserting a stem through an opening in a wall of the body cavity;
   receiving an instrument through a cap being disposed at a proximal end of the stem, through the stem, and into the body cavity, inserting the instrument through the stem comprising inserting the instrument through one of a plurality of channels formed by a partition positioned within a bore of the stem, the partition comprising a central portion and the plurality of channels each configured to receive an instrument of a plurality of instruments;
   inflating an instrument seal being disposed at a distal end of the stem to seal against an outer surface of the instrument and to inhibit fluid communication between the body cavity and a bore of the stem; and
   providing insufflation pressure to the body cavity through a conduit extending through the cap, the conduit comprising:
      an inlet being configured to be connected to a source of pressurized fluid; and
      a first outlet being configured to be in fluid communication with the body cavity after the stem is inserted through the opening in the body cavity.

2. The method of claim 1, wherein the instrument seal comprises a balloon.

3. The method of claim 2, wherein the balloon comprises a compliant wall at least partially defining an interior volume, and wherein the balloon is configured to retain pressurized fluid within the interior volume.

4. The method of claim 1, wherein inflating the instrument seal comprises holding the instrument in position with the instrument seal.

5. The method of claim 1, further comprising sealing an entry port of the cap to maintain insufflation pressure and inhibit contamination of the body cavity after inserting the stem through the opening in the wall of the body cavity.

6. The method of claim 1, wherein prior to inserting the stem, the instrument seal is configured to be in a deflated condition to facilitate insertion of the stem through the opening in the wall of the body cavity.

7. The method of claim 6, further comprising deflating the instrument seal prior to removing of the stem from the wall of the body cavity.

8. The method of claim 1, wherein the instrument comprises at least one of:
   an instrument configured to grasp, manipulate, cauterize, or cut tissue;
   an instrument configured to provide an interior view of the body cavity; or
   an instrument configured to provide or remove fluid from the body cavity.

9. A method of providing access for a medical procedure in a body cavity of a patient, the method comprising:

inserting a stem through an opening in a wall of the body cavity;

transitioning an inflatable annular retaining seal being disposed on the stem proximate to a cap of the stem between an expanded configuration and a retracted configuration to seal the opening in the wall of the body cavity, the cap being disposed at a proximal end of the stem, the inflatable annular retaining seal being in communication with a conduit being configured to facilitate transitioning the inflatable annular retaining seal between the expanded configuration and the retracted configuration, and transitioning an instrument seal being disposed at a distal end of the stem between an expanded configuration and a retracted configuration to seal against an outer surface of an instrument extending therethrough and to inhibit fluid communication between the body cavity and a bore of the stem, the instrument seal being in communication with the conduit being configured to facilitate transitioning the instrument seal between the expanded configuration and the retracted configuration, wherein the instrument seal extends radially outward from the stem in the expanded configuration.

10. The method of claim 9, wherein the instrument seal comprises a balloon.

11. The method of claim 9, wherein transitioning the instrument seal to the expanded configuration comprises holding the instrument in position with the instrument seal.

12. The method of claim 9, wherein transitioning the instrument seal to the expanded configuration comprises receiving pressurized fluid through an inlet of the conduit to transition the instrument seal.

13. The method of claim 12, wherein receiving pressurized fluid through the inlet of the conduit comprises injecting liquid solution through the inlet into the conduit, and wherein the conduit is configured to retain pressurized fluid within the instrument seal and the conduit once pressurized fluid is injected into the inlet.

14. The method of claim 12, further comprising connecting the conduit to a source of pressurized gas through the inlet.

15. The method of claim 9, further comprising providing insufflation pressure to the body cavity through an outlet of the conduit in fluid communication with the body cavity.

16. The method of claim 9, further comprising transitioning the instrument seal from the expanded configuration to the retracted configuration prior to removing the stem from the wall of the body cavity.

17. The method of claim 9, wherein the instrument seal comprises a generally toroidal shape when expanded.

18. The method of claim 17, wherein the stem is configured to accommodate a plurality of instruments within the bore, wherein the instrument seal comprises a plurality of bulged regions, and wherein each of the plurality of bulged regions is configured to seal against an outer surface of a respective instrument of the plurality of instruments such that the instrument seal is configured to provide increased force to hold each of the plurality of instruments within the bore when the instrument seal is expanded.

19. The method of claim 9, wherein the instrument comprises at least one of:

an instrument configured to grasp, manipulate, cauterize, or cut tissue;

an instrument configured to provide an interior view of the body cavity; or an instrument configured to provide or remove fluid from the body cavity.

* * * * *